United States Patent
Alexander et al.

(10) Patent No.: US 7,563,141 B2
(45) Date of Patent: Jul. 21, 2009

(54) IMPLANTABLE NEUROSTIMULATOR ADAPTERS

(75) Inventors: James A. Alexander, Shorewood, MN (US); Paulus C. van Venrooij, Hoensbroek (NL)

(73) Assignee: Medtronic, Inc., Minneapolis, MN (US)

(*) Notice: Subject to any disclaimer, the term of this patent is extended or adjusted under 35 U.S.C. 154(b) by 284 days.

(21) Appl. No.: 11/684,126

(22) Filed: Mar. 9, 2007

(65) Prior Publication Data

US 2008/0208302 A1      Aug. 28, 2008

Related U.S. Application Data

(63) Continuation-in-part of application No. 11/678,706, filed on Feb. 26, 2007.

(51) Int. Cl.
*A61N 1/375* (2006.01)
(52) U.S. Cl. .................................. 439/669; 607/37
(58) Field of Classification Search ............... 439/668, 439/669, 638; 607/36, 37, 38
See application file for complete search history.

(56) References Cited

U.S. PATENT DOCUMENTS

| | | | |
|---|---|---|---|
| 5,275,620 A | | 1/1994 | Darby et al. |
| 5,366,496 A | | 11/1994 | Dahl et al. |
| 5,679,022 A | * | 10/1997 | Cappa et al. ............... 439/502 |
| D525,708 S | | 7/2006 | Jones et al. |
| 7,128,600 B2 | | 10/2006 | Osypka |
| 7,242,987 B2 | * | 7/2007 | Holleman et al. ........... 607/122 |
| 2004/0034392 A1 | | 2/2004 | Spadgenske |
| 2004/0260355 A1 | | 12/2004 | Holleman et al. |
| 2005/0272280 A1 | | 12/2005 | Osypka |

FOREIGN PATENT DOCUMENTS

WO       9916503 A       4/1999

OTHER PUBLICATIONS

Medtronic, Inc., Neurostimulation System, Expanding the Array of Pain Control Solutions, Medtronic Brochure, 1999 (UC199901189EN NI-3764EN).

* cited by examiner

*Primary Examiner*—Neil Abrams
(74) *Attorney, Agent, or Firm*—Fredrikson & Byron, P.A.

(57) ABSTRACT

An adapter for coupling a pair of implantable neurostimulator lead extensions to a connector port of a neurostimulator device includes an elongate body, a connector including eight contacts coupled to a first end of the elongate body, and a housing, which includes two pairs of ports, coupled to a second end of the elongate body. A first pair of ports has openings located on a first face of the housing, and a second pair of ports has openings located on a second face of the housing, wherein the first face is opposite the second face. The adapter connector contacts provide for electrical coupling within the device port, and openings of each of the pairs of adapter housing ports are arranged to receive insertion of side-by-side connector terminals of a plug of each lead extension for electrical coupling within the ports.

44 Claims, 7 Drawing Sheets

IMPLANTABLE NEUROSTIMULATOR ADAPTERS

RELATED APPLICATION

The present patent application is a continuation-in-part of patent application Ser. No. 11/678,706 entitled IMPLANTABLE NEUROSTIMULATOR ADAPTERS, which was filed on Feb. 26, 2007, and is hereby incorporated, by reference, in its entirety.

TECHNICAL FIELD

The present invention pertains to extending implantable neurostimulator leads and more particularly to adapters for neurostimulator lead extensions.

BACKGROUND

Implantable neurostimulators can provide electrical stimulation for the treatment of pain and/or various neurological disorders. Neurostimulators typically include one or more stimulation electrodes which may be implanted at specific sites along a spinal cord, a peripheral nerve, or in a brain of a patient; the one or more electrodes are typically mounted to an elongate lead body which carries corresponding conductors for electrical coupling of the electrodes to a neurostimulator device. Because the neurostimulator device is usually implanted in a subcutaneous pocket that is somewhat remote from the stimulation site, often times a lead extension is required to couple a lead connector, which terminates a proximal end of the lead body, to the device. The extension provides an additional length of conductor(s) to reach the device for the electrical coupling of the one or more lead electrodes. One or more connector terminals terminating a proximal end of the lead extension are configured to mate with corresponding connector ports of the device.

In recent years, new models of neurostimulator devices have been developed for increased functionality; modifications to the size and/or shape of these newer devices have been made, for example, to accommodate additional components, while keeping a bulk of the devices to a minimum. In many instances, the modifications have been accompanied by changes to the configuration of the connector ports of these devices so that the ports are no longer compatible with connector terminals of lead extensions which were designed to couple with older style devices. Thus, for those patients who either require or desire that an older style device be exchanged for a newer device, there is a need for an adapter to couple the connector terminals of one or more previously implanted lead extensions to one or more ports of the newer device.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
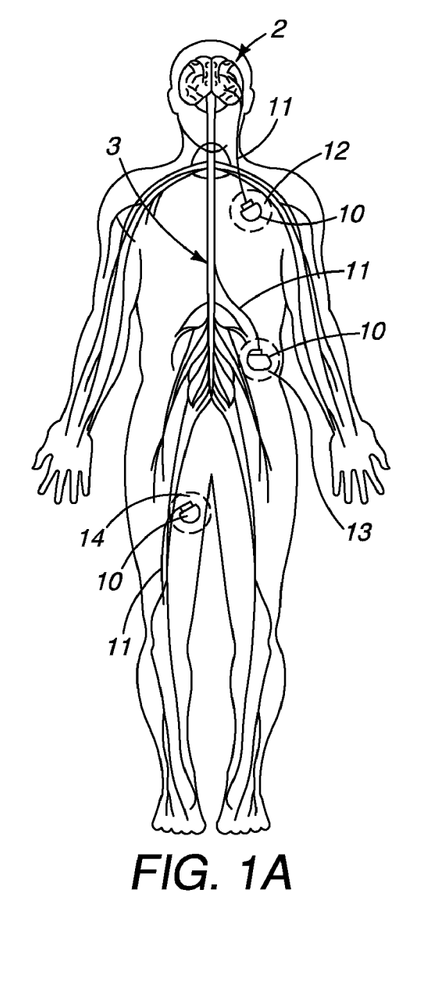
FIG. 1A is schematic plan view of a human body showing various general implant locations for implantable neurostimulator systems.

FIG. 1A is schematic plan view of a human body showing various general implant locations for implantable neurostimulator systems. FIG. 1A illustrates three general types of neurostimulator systems including devices 10 each coupled to an elongate lead 11. A first of devices 10 is shown implanted in a pectoral region 12, for example, within a subcutaneous pocket, and corresponding lead 11 extending from device 10 to a site within a brain 2; a second of devices 10 is shown implanted in a lower region 13 of the body, and corresponding lead 11 extending from device 10 to a site along a spinal cord 3; a subcutaneous pocket in lower region 13 may be formed, in an anterior, abdominal area of the body, or in a posterior, high buttocks area of the body. A third of devices 10 is shown implanted in a subcutaneous pocket form in a thigh region 14 of the body, and a corresponding lead 11 is shown extending from device 10 to a peripheral nerve site in a leg of the body. It should be noted that any of the pockets in regions 12, 13, 14 may hold a device coupled to a lead extending to any of the peripheral nerves, for example, in either leg, in either arm, or in the neck or head. Although not shown, those skilled in the art will understand that leads 11 each include one or more electrodes in proximity to a distal end thereof.

Figure 1B:
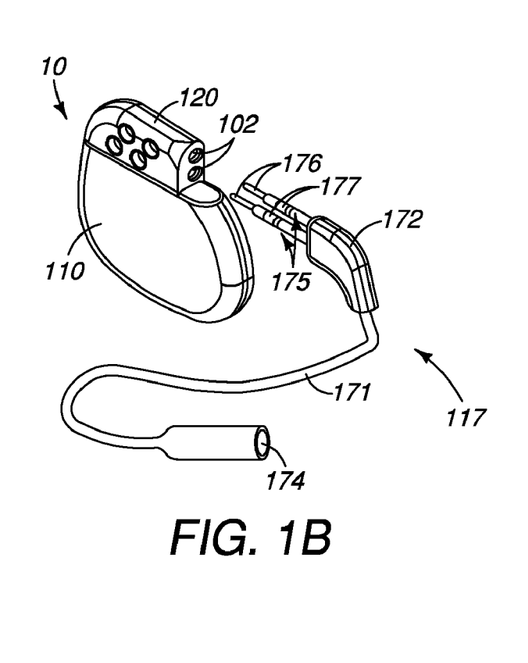
FIG. 1B is a perspective view of a portion of an exemplary implantable neurostimulator.

As previously described, a length of each of leads 11 may be extended by a lead extension. FIG. 1B is a perspective view of device 10 and an exemplary lead extension 117. FIG. 1B illustrates device 10 including a housing or can 110 and a connector module 120 coupled to can 110 and including two connector ports 102; can 110 houses a battery and electronic circuitry necessary to provide electrical stimulation delivered by the electrodes of leads 11. Those skilled in the art understand that electrical contacts within each of ports 102 are electrically coupled, via hermetically sealed feedthroughs, to the electrical circuitry housed within can 110. FIG. 1B further illustrates lead extension 117 including an elongate body 171, to which a plug 172 is coupled at a proximal end, and to which a connector port 174 is coupled at a distal end. A pair of connector terminals 175 is shown extending proximally from plug 172; each of connector terminals 175 includes a terminal pin contact 176 and a contact surface 177, which is spaced apart from pin contact 176 along a length of the corresponding connector terminal 175.

According to the illustrated embodiment, ports 102 of device connector module 120 are positioned to receive, for electrical and mechanical coupling, the pair of side-by-side connector terminals 175, and, extension connector port 174 is adapted to receive, for electrical and mechanical coupling, a lead connector, for example, an in-line connector, such as is known to those skilled in the art, which terminates a proximal end of the lead and includes a plurality of spaced apart contacts. Those skilled in the art will appreciate that extension port 174 includes a plurality of electrical contacts, which couple with the contacts of the lead connector, when the connector is fully inserted in port 174, and which are each coupled either to a corresponding terminal pin contact 176 or to a corresponding contact surface 177 of connector terminals 175, via a corresponding elongate conductor extending within elongate body 171. Thus, when connector terminals 175 are fully inserted into device ports 102, and the lead connector is fully inserted into extension portion 174, electrical stimulation therapy may be delivered from device 10 to the one or more electrodes of lead 11, either implanted in brain 2, along spinal cord 3, or along a peripheral nerve (FIG. 1A).

Figure 2A:
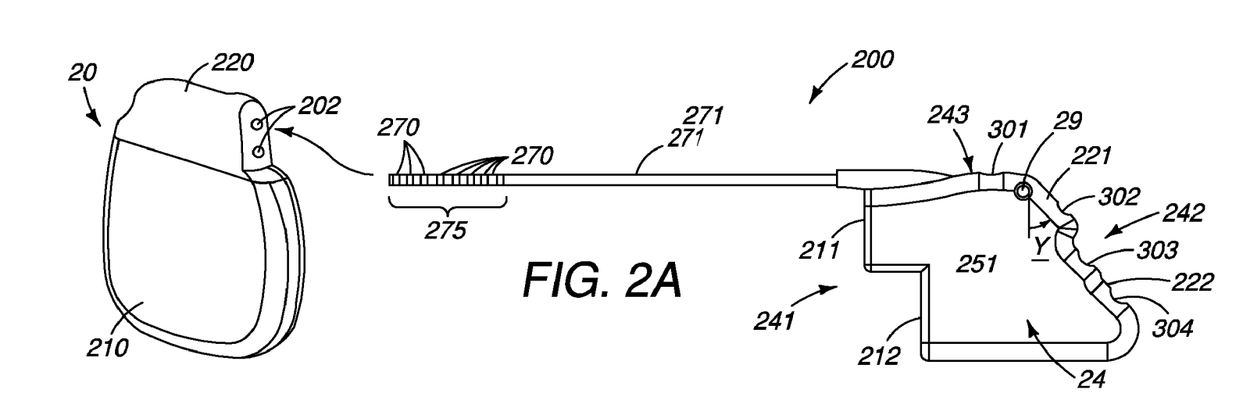
FIG. 2A is a combination plan view and perspective view of a neurostimulator adapter and a corresponding neurostimulator device, respectively, according to some embodiments of the present invention.
Figure 2B:
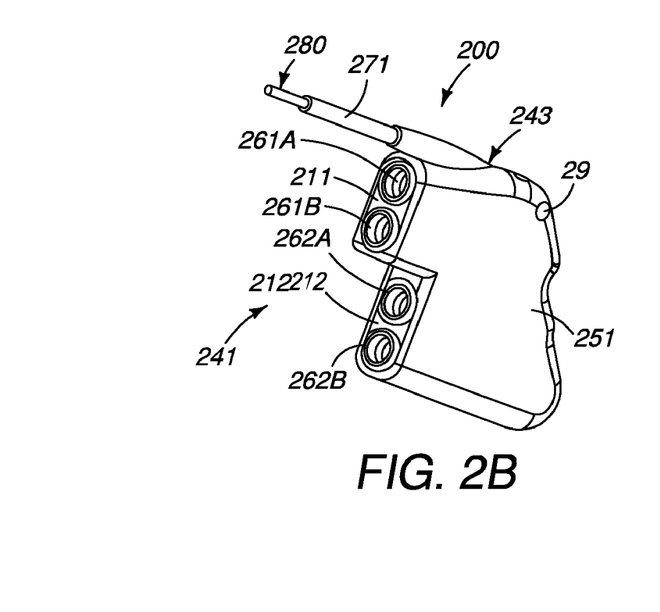
FIG. 2B is a perspective view of a portion of the adapter shown in FIG. 2A, according to some embodiments.

FIG. 2A is a combination plan view and perspective view of a neurostimulator adapter 200 and a neurostimulator device 20, respectively, according to some embodiments of the present invention; and FIG. 2B is a perspective view of a portion of adapter 200. FIG. 2A illustrates device 20, like device 10 (FIG. 1B), including a housing or can 210 and a connector module 220, however connector module 220 includes ports 202 which differ in individual size and configuration from ports 102 of device 10. According to embodiments of the present invention, when device 10 (FIG. 1B) is changed out for device 20, an adapter, for example, adapter 200, is necessary to provide a compatible coupling between one of ports 202 of device 20 and the previously implanted extension 117.

With reference to FIG. 2A, adapter 200 includes an elongate body 271 to which a connector 275, which is compatible with each of ports 202 of device 20, is coupled; connector 275 is shown including eight contacts 270, so it should be appreciated that each of ports 202 include a corresponding set of eight device contacts for electrical coupling with contacts 270, when connector 275 is fully inserted therein. FIG. 2A further illustrates adapter 200 including a housing 24 coupled to a distal end of body 271; with reference to FIG. 2B, housing 24 includes a first pair of ports 261A, 261B and a second pair of ports 262A, 262B, wherein each pair of ports is adapted to receive the pair of connector terminals 175 of extension 117 (FIG. 1B). Although the figures illustrate a preferred adapter embodiment including four ports for coupling with a pair of lead extensions 117, it should be noted that the scope of the invention is not so limited; for example, an alternate embodiment of the present invention includes an adapter housing including only one pair of ports and a corresponding connector including only four contacts.

According to the illustrated embodiment, a group of eight conductors 280 (FIG. 2B) extends within body 271 between connector 275 and housing 24; each of the eight conductors 280, for example, individually insulated cable conductors, provide for electrical coupling between a contact 270 and a corresponding housing contact, each of which is disposed within one of ports 261A,B, 262A,B and will be described in greater detail below. Conductors 280 may extend within body 271 in either a straight or coiled configuration, and body 271 may include either a single or multi-lumen tube, for example, formed by an extrusion and/or molding process from medical grade silicone, or polyurethane, or a combination thereof. Conductors 280 are preferably formed from an MP35N alloy, which is known to those skilled in the art; and each of conductors 280 is coupled to a corresponding connector contact 270 by means known to those skilled in the art, for example, crimping and/or welding; and each of conductors 280 is preferably individually insulated by an insulative jacket, for example, formed from a fluoropolymer or a polyimide.

FIGS. 2A-B further illustrate housing 24 including a first sidewall 251, a second sidewall 252 (opposite first sidewall 251—seen in FIG. 2C), a first face 241, which extends between sidewalls 251, 252 and on which openings of ports 261A,B, 262A,B are located, a second face 242 (opposite first face 241), and a third face 243, which extends between first face 241 and second face 242. According to the illustrated embodiment: first and second sidewalls 251, 252 each include a relatively flat outer surface extending alongside each of ports 261A,B, 262A,B; first face 241 includes a first portion 211, on which openings of ports 261A, B are located, and a second portion 212 recessed from first portion 211, on which openings of ports 262A, B are located; and, second face 242 extends at an angle Y, for example, greater than 0 degrees and less than 90 degrees, with respect to first face 241, and includes a first portion 221 and a second portion 222 recessed from first portion 221. FIGS. 2A-B further illustrate adapter housing 24 including a hole 29, which extends through housing 24 from first sidewall 251 to second sidewall 252, and is located in proximity to an intersection of second housing face 242 and third housing face 243. Hole 29 may be used to facilitate securing, for example, via a suture, of adapter housing 24 to tissue within an implant pocket, either alongside device 20 or separate from device 20.

Figure 2C:
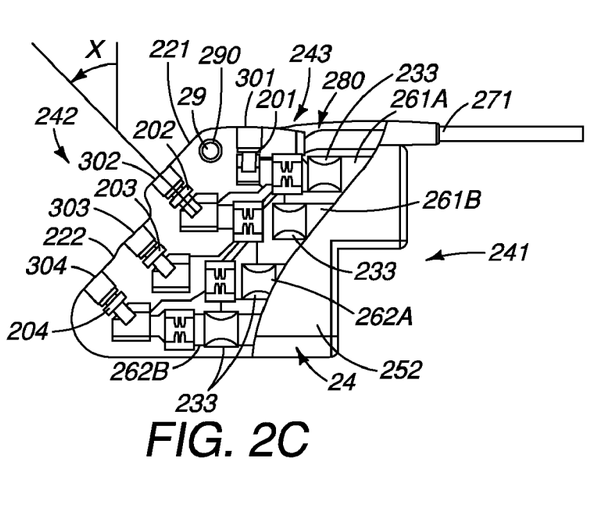
FIG. 2C is a plan view including a partial cut-away section of the adapter shown in FIG. 2A, according to some embodiments.

FIG. 2C is a plan view of a portion of adapter 200 including a partial cut-away section of adapter housing 24, according to some embodiments of the present invention. FIG. 2C illustrates each of ports 261A,B, 262A,B including a spring-type housing contact 233, for example, a multi-beam contact, which may be formed from stainless steel, MP35N alloy, titanium or any other suitable material known to those skilled in the art, and a set screw-type housing contact, which may likewise be formed from stainless steel, MP35N alloy, titanium or any other suitable material known to those skilled in the art, and which includes a set screw 301, 302, 303, 304 mounted in a set screw block. FIG. 2C further illustrates a shaft of set screw 201 extending approximately parallel with first face 241 of housing 24, while shafts of each of set screws 202, 203 and 204 extend at an angle X, for example, greater than 0 degrees and less than 90 degrees, with respect to first face 241. An access port 301 for set screw 201 is shown located on third face 243; an access port 302 for set screw 202 is shown located on first portion 221 of second face 242; and access ports 303, 304 for set screws 203 and 204, respectively, are shown located on second portion 222 of second face 242. Those skilled in the art will understand that access ports 301, 302, 303 and 304 provide access for a set screw wrench, to engage screws 201, 202, 203, 204, yet are sealed to prevent ingress of bodily fluids when adaptor 200 is implanted; any suitable type of grommet known to those skilled in the art and through which a set screw wrench may pierce, may be employed by embodiments of the present invention. With reference to FIG. 2C, it may be appreciated that the angled arrangement of set screws 202, 203, 204, in combination with the angling and contour of second face 242, contributes to a reduction in a bulk of housing 24 from a bulk that would have resulted if set screws 202, 203, 204 had been oriented in a traditional manner, for example, like set screw 201, such that their shafts extended parallel to first face 241. Such a traditional arrangement of set screws 202, 203, 204 would have forced an increased footprint of housing 24, for example, along second face 242 (to provide appropriately oriented access ports for the set screws along second face 242), or would have forced an increased thickness of housing 24, between sidewalls 251, 252 (to provide appropriately oriented access ports along one or both of sidewalls 251, 252).

With reference back to FIG. 1B, it will be appreciated that, when each connector terminal 175 of extension plug 172 is fully inserted into a corresponding port of one of the pairs of ports 261A,B, 262A,B, each contact surface 177 mates with a corresponding spring contact 233 and each terminal pin contact 176 is positioned to mate with a corresponding set screw 301, 302, 303, 304. It should be noted that the scope of the present invention is not limited to the illustrated types of contacts and alternate embodiments of the present invention may include any other types of contacts known to those skilled in the art. Although not labeled in FIG. 2C, those skilled in the art will recognize a set of sealing rings shown in each of ports 261A,B, 262A,B; the illustrated sealing rings are intended to provide electrical isolation between each pin contact 176 and corresponding contact surface 177 of fully inserted terminals 175, but are not necessary elements for every embodiment of the present invention.

FIG. 2C further illustrates conductors 280 extending from body 271 into housing 24, beneath third face 243 of housing 24, and conductor paths (not labeled) extending within housing from each of housing contacts 233, 301, 302, 303, 304 toward third face 243. Those skilled in the art will appreciate that each conductor 280 may be electrically coupled to a corresponding housing contact in a number of ways; for example, each conductor 280 may be routed into housing 24 along a corresponding conductor path for direct coupling with the corresponding contact, for example, via welding, or, a separate conductor may extend from each contact, along the corresponding conductor path to a corresponding coupling plate located in proximity to third face 243 for coupling to the corresponding conductor 280, for example, via welding. Those skilled in the art will further appreciate that appropriate electrical isolation may be provided for each conductor within housing 24, either via an insulative jacket formed about each conductor, or via insulative walls formed within housing 24 between each conductor, or via a combination thereof.

According to an exemplary embodiment of the present invention, housing 24 is formed from medical grade silicone, preferably having a durometer of approximately 65D. With reference to FIG. 2C, a reinforcing tubing or liner 290 that extends within hole 29 may be desirable, particularly when housing 24 is formed from a relatively soft material that requires a harder interface, for example, for a suture to bear against; examples of appropriate materials for liner 290 include, without limitation, polysulfone and a relatively hard durometer of polyurethane, for example, 75D. Housing 24 may be molded and the illustrated components assembled therein according to any suitable method known to those skilled in the art. According to an exemplary assembly method, a portion of housing 24 is molded with openings into which the components are inserted; conductors may be coupled to each of the housing contact components either before or after insertion into the corresponding opening of the corresponding housing. After the conductors are routed along the conductor paths, voids over and around each opening are filled in, either by a secondary molding process or manual injection of filler material, for example, medical grade silicone.

Figures 3A, 3B, 3C:
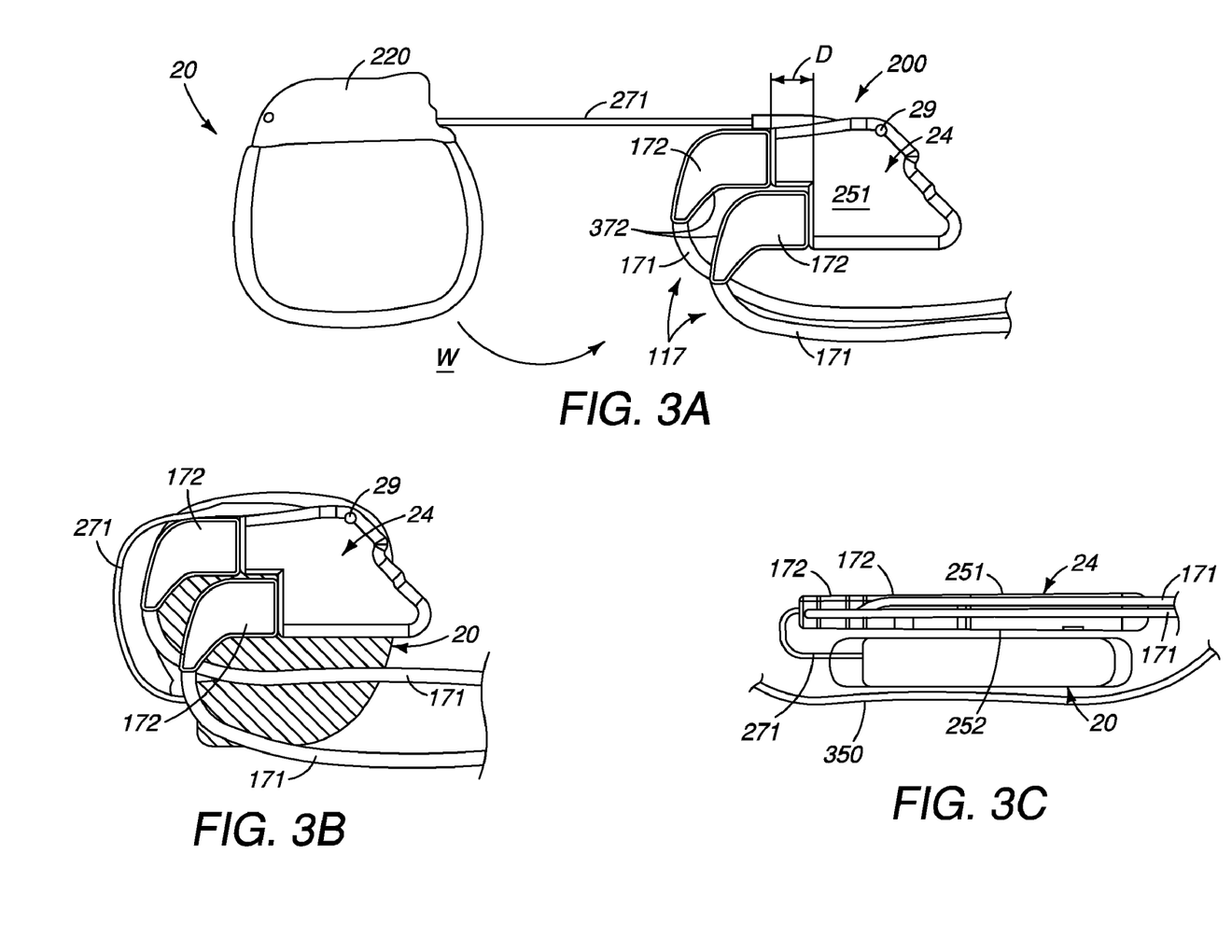
FIG. 3A is a plan view of a portion of a system including the adapter and device of FIG. 2A, according to some embodiments of the present invention.
FIG. 3B is a plan view of an exemplary implant configuration for the portion of the system shown in FIG. 3A.
FIG. 3C is an end view of the system configured as in FIG. 3B.

FIG. 3A is a plan view of a portion of a system including device 20, two extensions 117 (FIG. 1B), and adapter 200, which couples extensions 117 to device 20, according to some embodiments of the present invention. It should be noted that, although device 20 has been illustrated having two connector ports 202, device need only have one of these ports 202. FIG. 3A illustrates extension connector 275 (FIG. 2A) inserted into device connector module 220, and each extension plug 172 plugged into adapter housing 24. With reference to FIG. 3A, in conjunction with FIG. 2A, it may be appreciated that, according to a preferred embodiment, second portion 212 of first housing face 241 is recessed from first portion 211 of first face 241 by a distance D that allows for surfaces 372 of extension plugs 172 to be spaced apart from one another when connector terminals 175 (FIG. 1B) are fully inserted into corresponding ports 261A,B, 262A,B (FIG. 2B) of adapter housing 24.

According to some exemplary implant methods, extensions 117 are plugged into adapter 200, either before or after adapter 200 is plugged into device 20, and then device 20 is rotated around, per arrow W, and shifted alongside adapter 200 and extension plugs 172 such that elongate body 271 of adapter 200, which extends from housing 24 in a same general direction that openings of ports 261A,B, 262A,B face (FIG. 2B), wraps alongside plugs 172, for example, as is shown in FIG. 3B. A length of elongate body 271 may be between approximately 10 centimeters and approximately 20 centimeters to accommodate such an implant configuration. It should be noted that, due to the flexible nature of adapter body 271 and extension bodies 171, in practice, the positions and contour of each, along with positions of housing 24 and plugs 172, would not be limited to the illustrated configuration. An implanter may desire to secure, for example, with a suture through hole 29, adapter housing 24 to subcutaneous tissue within an implant pocket alongside device 20 such that adapter housing 24 will remain behind device 20 in the pocket, that is, at a deeper location in the body, for example, as illustrated in FIG. 3C, where item number 350 represents an exterior of the body, or skin. Such an arrangement is preferred if a battery of device 20 has the capacity to be re-charged transcutaneously, and for added protection of adapter 200 and extensions 117 from nicks and cuts, if, and when and explant of device 20 is required, at a later date. With further reference to FIG. 3C, in conjunction with FIG. 2B, it may be appreciated that a maximum thickness of housing 24, as defined between outer surfaces of sidewalls 251, 252, is kept to a minimum by the arrangement of ports 261A,B, 262A,B and set screws 201, 202, 203, 204, as previously described; according to exemplary embodiments, the maximum thickness of housing 24 is no greater than approximately 0.3 inch, preferably being between approximately 0.22 inch and approximately 0.27 inch.

According to alternate implant methods, adapter 200 may be implanted in a first subcutaneous pocket and device 20 in a second subcutaneous pocket; for example, the first pocket may be one previously formed for a device which has been explanted to be exchanged for device 20, and the second pocket, a new pocket formed for device 20. With reference back to FIG. 1A, the first pocket may be in pectoral region 12 and the second pocket in lower region 13 or thigh region 14. For such an implant configuration, in which there is a relatively significant distance between the two pockets, a length of adapter body 271 may be greater than approximately 40 centimeters, upwards to approximately 110 centimeters.

Figure 4A:
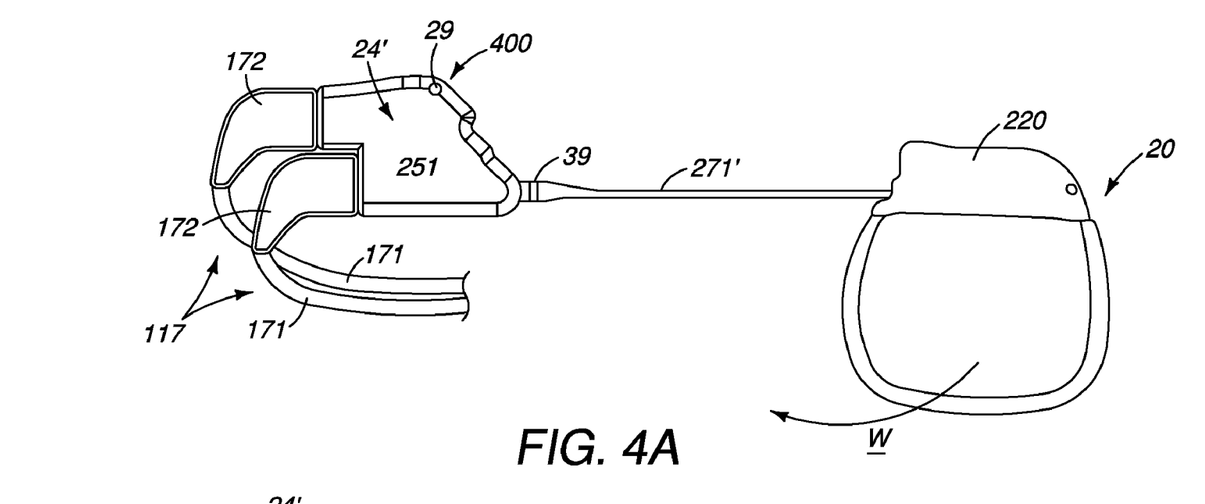
FIG. 4A is a plan view of a portion of a system including an adapter, according to an alternate embodiment of the present invention.
Figure 4B:
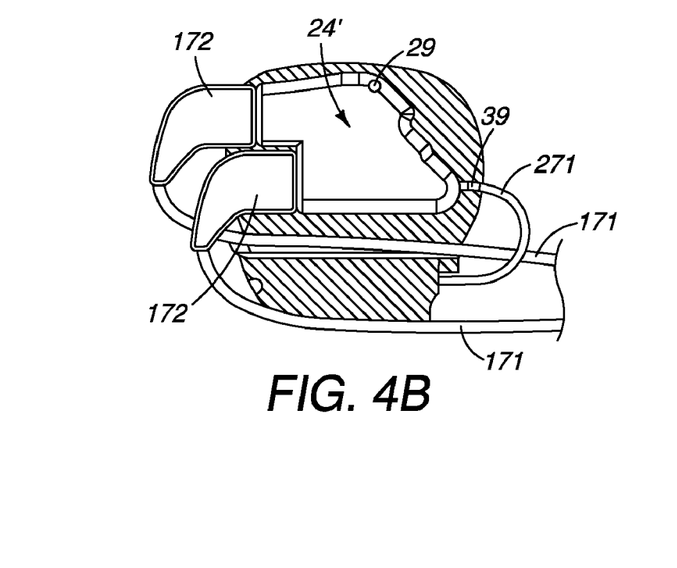
FIG. 4B is a plan view of an exemplary implant configuration for the portion of the system shown in FIG. 4A.
Figure 4C:
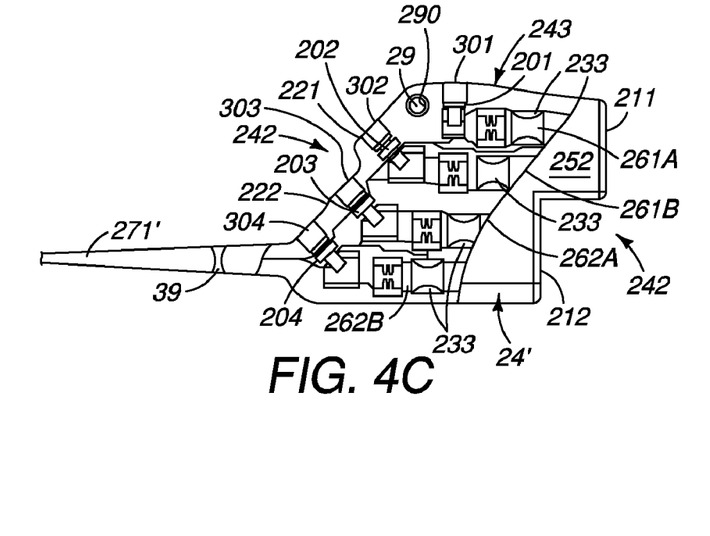
FIG. 4C is a plan view including a cut-away section of the adapter shown in FIGS. 4A-B, according to some embodiments.

FIG. 4A is a plan view of a portion of another system including device 20, two extensions 117 and an adapter 400, which couples extensions 117 to device 20, according to alternate embodiments of the present invention. FIG. 4B is a plan view of an exemplary implant configuration for the portion of the system shown in FIG. 4A; and FIG. 4C is a plan view including a cut-away section of adapter 400. FIGS. 4A-C illustrate adapter 400 including a housing 24' coupled to a first end of an elongate body 271'; and, although not seen, it should be understood that a connector, similar to connector 275 (FIG. 2A-*previously* described for adapter 200), is coupled to a second end of body 271', which is shown (FIG. 4A-B) inserted within one of ports 202 of device header 220. Although not shown, conductors 280 extend within body 271', which may be of similar in length and construction as that previously described for body 271 of adapter 200. According to the illustrated embodiment, adaptor 400, like adapter 200, includes first and second pairs of ports 261A,B, 262A,B, each of which receive a corresponding connector terminal 175 (FIG. 1B) of extension plugs 172; furthermore, like housing 24 of adapter 200, housing 24' of adapter 400 includes first and second sidewalls 251, 252, first face 241 on which openings of ports 261A,B, 262A,B are located, second face 242 on which access ports 302, 303, 304 for set screws 202, 203, 204, respectively, are located, and third face 243 on which access port 301 for set screw 201 is located. Adapter housing 24' differs from adapter housing 24, in that elongate body 271' extends from second face 242 of housing 24' in a direction which is approximately opposite to a general direction in which each of the openings of ports 261A,B, 262A,B face. Comparing FIG. 4C with FIG. 2C, it should be noted that, aside from conductor routing toward that portion of second face 242 from which body 271' extends, the arrangement of ports 261A,B, 262A,B and contacts 233, 201, 202, 203, 204 within housing 24' of adapter 400 is very similar to that for housing 24 of adapter 200. Thus, it may be appreciated that a bulk of adapter housing 24' does not differ significantly, in footprint or thickness, from that of adapter housing 24.

FIGS. 4A-B further illustrate an exemplary implant method, wherein device 20 is rotated around, per arrow W, and shifted alongside adapter 400 and extension plugs 172 such that adapter body 271' wraps alongside device 20. As previously noted, in conjunction with FIG. 3B, due to the flexible nature of adapter body 271' and extension bodies 171, in practice, the positions and contour of each, along with positions of housing 24' and plugs 172, would not be limited to the configuration illustrated in FIG. 4B. FIGS. 4A-C further illustrates elongate body 271' including a thickened or reinforced zone, in proximity to housing 24', wherein a groove 39 is formed; the thickened portion and associated groove 39 may be used to accommodate a suture for securing of adapter 400 to subcutaneous tissue. Alternate implant arrangements of device 20 and extensions 117 coupled together by adapter 400 may include those as previously described for device 20 and extensions 117 coupled together by adapter 200.

Figure 5A:
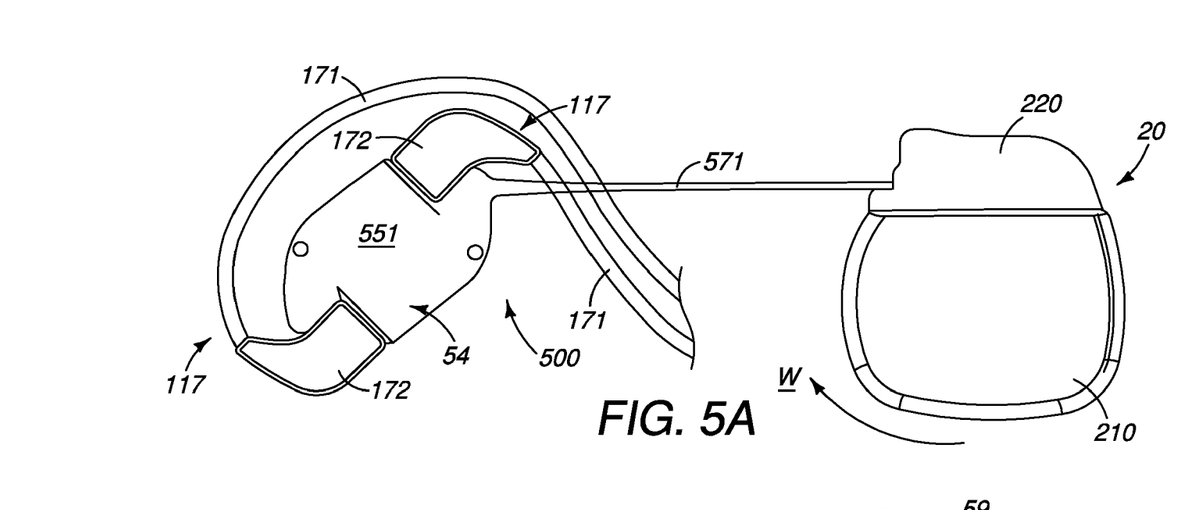
FIG. 5A is a plan view of a portion of a system including an adapter, according to another alternate embodiment of the present invention.
Figure 5B:
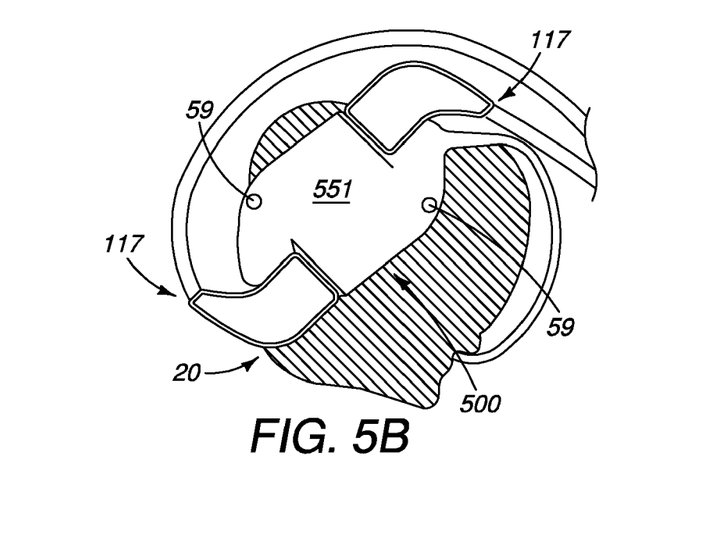
FIG. 5B is a plan view of an exemplary implant configuration for the portion of the system shown in FIG. 5A.
Figure 5C:
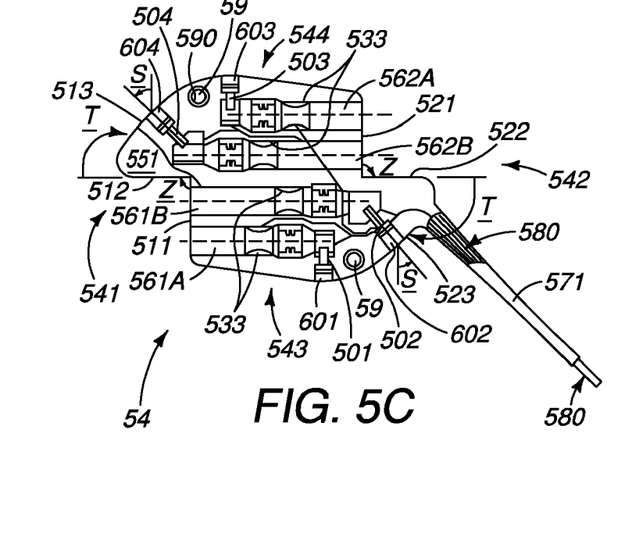
FIG. 5C is a plan view including a cut-away section of the adapter shown in FIGS. 5A-B, according to some embodiments.
Figure 5D:
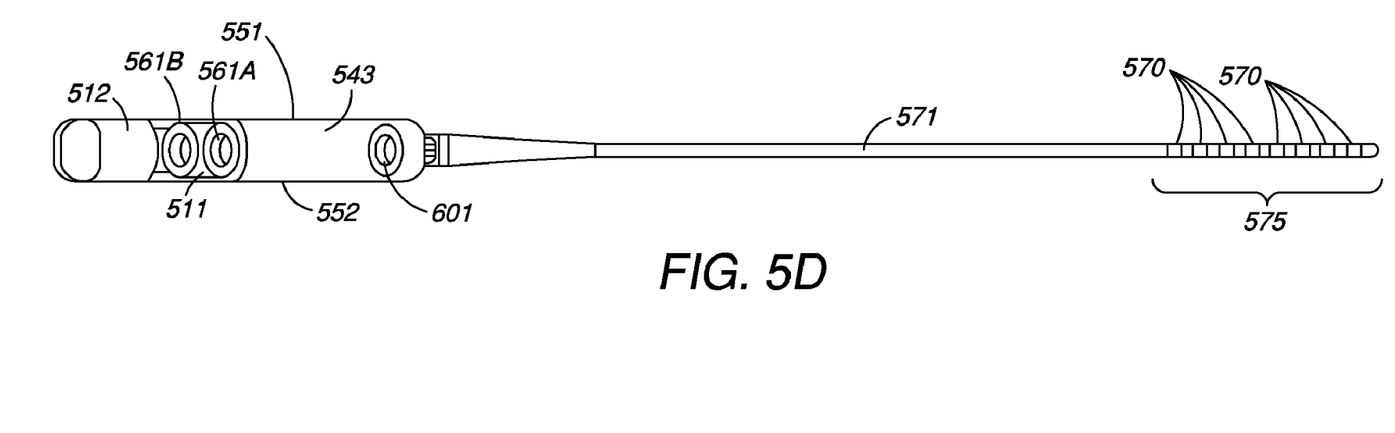
FIG. 5D is a bottom plan view of the adapter shown in FIGS. 5A-B, according to some embodiments.

FIG. 5A is a plan view of a portion of another system including an adapter 500 coupling two extensions 117 (FIG. 1B) to device 20, according to other alternate embodiments of the present invention; and FIG. 5B is a plan view of an exemplary implant configuration for the portion of the system shown in FIG. 5A. FIG. 5C is a plan view including a cut-away section of adapter 500, according to some embodiments; and FIG. 5D is a bottom plan view of adapter 500. FIGS. 5A-D illustrate adapter 500 including an elongate body 571 and a housing 500 coupled to a distal end of body 571; a connector 575 including eight connector contacts 570 (FIG. 5D) is coupled to a proximal end of body 571 for electrical coupling with device contacts, when connector 575 is inserted into one of ports 202 of device connector module 220 for electrical coupling, as is illustrated in FIGS. 5A-B. FIGS. 5A-B further illustrate connector terminals 175 (FIG. 1B) of each extension plug 172 inserted into adapter housing 54 for electrical coupling.

FIG. 5C illustrates housing 54 including a first pair of ports 561A,B, which have openings on a first face 541 of housing 54 to receive connector terminals 175 of one of plugs 172, and a second pair of ports 562A,B, which have openings on a second face 542 of housing 54 to receive connector terminals 175 of another of plugs 172. FIG. 5C further illustrates each of ports 561A,B, 562A,B including a spring-type housing contact 533, similar to previously-described contact 233 of adapter 200, and a set screw-type housing contact, also similar to that previously described, which includes a set screw 501, 502, 503, 504 mounted in a set screw block. It should be appreciated that, when each connector terminal 175 of extension plug 172 is fully inserted into a corresponding port of one of the pairs of ports 561A,B, 562A,B, each contact surface 177 mates with a corresponding spring contact 533 and each terminal pin contact 176 is positioned to mate with a corresponding set screw 501, 502, 503, 504. It should be noted again that the scope of the present invention is not limited to the illustrated types of contacts and alternate embodiments of the present invention may include any other types of contacts known to those skilled in the art. Although not labeled in FIG. 5C, those skilled in the art will recognize a set of sealing rings shown in each of ports 561A,B, 562A,B; the illustrated sealing rings are intended to provide electrical isolation between each pin contact 176 and corresponding contact surface 177 of fully inserted terminals 175, but are not necessary elements for every embodiment of the present invention.

With reference to FIGS. 5C-D, it should be appreciated that each housing contact 533, 501, 502, 503, 504 is electrically coupled to a corresponding connector contact 570 by one of eight elongate conductors 580, for example, individually insulated cable conductors, that extend within body 571 between housing 54 and connector 575. Conductors 580 may extend within body 571 in either a straight or coiled configuration, and body 571 may include either a single or multi-lumen tube, for example, formed by an extrusion and/or molding process from medical grade silicone, or polyurethane, or a combination thereof. Conductors 580 are preferably formed from an MP35N alloy, which is known to those skilled in the art; and each of conductors 580 is coupled to a corresponding connector contact 570 by means known to those skilled in the art, for example, crimping and/or welding; and each of conductors 580 is preferably individually insulated by an insulative jacket, for example, formed from a fluoropolymer or a polyimide. FIG. 5C illustrates conductors 580 extending from body 571 into housing 54, at a junction between body 571 and housing 54, and conductor paths (not labeled) extending within housing 54 from each of housing contacts 533, 501, 502, 503, 504 toward the junction. Each conductor 580 may be electrically coupled to a corresponding housing contact in a number of ways, some of which include those previously described for adapter 200.

FIGS. 5C-D further illustrate housing 54 including a first sidewall 551 and a second sidewall 552, between which first face 541 and second face 542 extend, and a third face 543, which extends between first and second faces 541, 542, and a fourth face 544, opposite third face 543, which also extends between first and second faces 541, 542. According to the illustrated embodiment first and second housing faces 541, 542 each include a first portion 511, 521, on which openings of corresponding ports 561A,B, 562A,B are located, a second portion 512, 522, and a third portion 513, 523; second portions 512, 522 of first and second housing faces 541, 542, respectively, project out from respective first portions 511, 521 at an angle Z, which is approximately 90 degrees; and third portions 513, 523 of first and second housing faces 541, 542, respectively, recede from respective second portions 512, 522 at an angle T, which is greater than 90 degrees and less than 180 degrees. Housing 54 may be formed from medical grade silicone in a manner similar to that described above for housing 24 of adapter 200.

FIG. 5C further illustrates a shaft of set screw 501 extending approximately parallel with first portion 511 of first housing face 541, a shaft of set screw 503 extending approximately parallel with first portion 521 of second housing face 542, a shaft of set screw 502 extending at an angle S, for example, greater than 0 degrees and less than 90 degrees, with respect to first portion 511, and a shaft of set screw 504 extending at angle S with respect to first portion 521. An access port 601 for set screw 501 is shown located on third face 543; an access port 602 for set screw 502 is shown located on third portion 523 of second face 542; an access port 603 for set screw 503 is shown located on fourth face 544; and an access port 604 for set screw 504 is shown located on third portion 513 of first face 541. Those skilled in the art will understand that access ports 601, 602, 603 and 604 provide access for a set screw wrench, to engage screws 501, 502, 503, 504, yet are sealed to prevent ingress of bodily fluids when adaptor 500 is implanted; any suitable type of grommet known to those skilled in the art and through which a set screw wrench may pierce, may be employed by embodiments of the present invention.

With reference to FIG. 5C, it may be appreciated that the angled arrangement of set screws 502 and 504, in combination with the angling of third portions 513, 523 of first and second housing faces 541, 542, respectively, contributes to a reduction in a bulk of housing 54 from a bulk that would have resulted if set screws 502, 504 had been oriented in a traditional manner, for example, like set screws 501 and 503, such that their shafts extended parallel to first portions 511, 521 of first and second housing faces 541, 542, respectively. Such a traditional arrangement of set screws 502, 504 would have forced an increased footprint of housing 54, for example, along first and second faces 541, 542 (to provide appropriately oriented access ports for the set screws along third and fourth faces 543, 544), or would have forced an increased thickness of housing 54, between sidewalls 551, 552 (to provide appropriately oriented access ports along one or both of sidewalls 551, 552). With reference to FIG. 5D, it may be appreciated that sidewalls 551, 552, according to the illustrated embodiment, have relatively flat outer surfaces extending alongside all of housing ports 561A,B, 562A,B. According to exemplary embodiments of the present invention, a maximum thickness between sidewall 551 and sidewall 552 is no greater than approximately 0.3 inches, preferably between approximately 0.22 and approximately 0.27 inches.

Referring now to FIGS. 5A-B, it should be appreciated that some implant methods for the illustrated system are similar to those described for the system including adapter 200 as shown in FIGS. 3A-B. Like adapter 200, a length of elongate body 571 of adapter 500 may be between approximately 10 centimeters and approximately 20 centimeters, to accommodate the implant configuration illustrated in FIG. 5B. If adapter 500 is implanted in a separate pocket from device 20, wherein there is some distance between the two pockets, for example, between pectoral region 12 and lower region 13 or thigh region 14, as previously described, the length of body 571 may be greater than 40 centimeters, upwards to approximately 110 centimeters. With further reference to FIGS. 5A-B, it will be appreciated that when connector terminals 175 of plugs 172 are inserted into housing 54, second portions 512, 522 of first and second housing faces 541, 542, respectively, each form a shelf-like projection, extending alongside the corresponding plug 172; this interface between each plug 172 and housing 54 may lend some stability to electrical connections of the inserted connector terminals 175.

As previously described for adapter 200, adapter 500 may be secured to subcutaneous tissue within the pocket by a securing element, for example, a suture, passed through a hole 59 of housing 54, which hole 59 extends from first sidewall 551 to second sidewall 552. Although FIGS. 5A-C show adapter housing 54 including two holes 59, one or both of holes 59 is/are optional and, if present, may be located elsewhere on housing 54. According to an exemplary embodiment that includes at least one of holes 59, and wherein housing 54 is formed from a relatively soft material such as silicone, a reinforcing tubing or liner 590 (FIG. 5C) extends within hole(s) 59; as previously described for hole 29 of adapter 200; examples of an appropriate material for liner 590 include, without limitation, polysulfone and a relatively hard durometer polyurethane, for example, 75D.

Figures 6A, 6B:
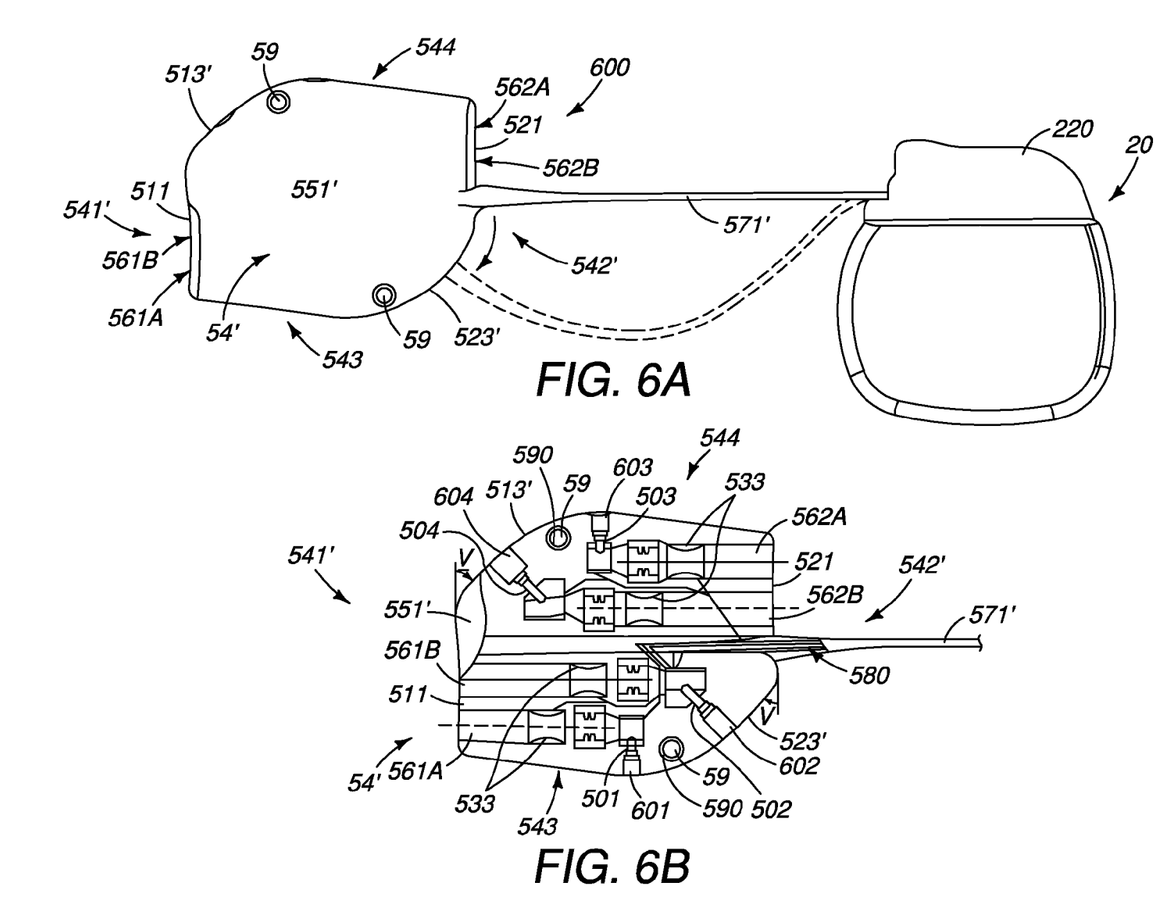
FIG. 6A is a plan view of a portion of a system including an adapter, according to yet another alternate embodiment of the present invention.
FIG. 6B is a plan view including a cut-away section of the adapter shown in FIG. 6A, according to some embodiments.

FIG. 6A is a plan view of a portion of a system including an adapter 600, according to yet another alternate embodiment of the present invention; and FIG. 6B is a plan view including a cut-away section of adapter 600, according to some embodiments. FIGS. 6A-B illustrate adapter 600 including a housing 54' coupled to a distal end of an elongate body 571'; and, although not seen, it should be understood that a connector, similar to connector 575 (FIG. 5D), is coupled to a second end of body 571', which is shown (FIG. 6A) inserted within one of ports 202 of device header 220. According to the illustrated embodiment, adaptor 600 is very similar to adapter 500, in that adapter 600 includes first and second pairs of ports 561A, B, 562A,B, each of which to receive a corresponding connector terminal 175 (FIG. 1B) of a corresponding extension plug 172, and housing contacts 533, 501, 502, 503, 504, which are arranged in generally the same way. Adapter housing 54' differs from adapter housing 54, in that housing 54' includes a first face 541' and a second face 542', which faces 541', 542' each only include two portions (comparable to previously described first portions 511, 521 and third portions 513, 523), such that a footprint of housing 54', for example, defined by a perimeter of a sidewall 551' of housing 54', is reduced from that defined by a perimeter of sidewalls 551, 552 of housing 54; a second portion 513', 523' of each of housing faces 541', 542' recedes from the corresponding first portion 511, 521 at an angle V (FIG. 6B), which is greater than 0 degrees and less than 90 degrees. According to an exemplary embodiment, housing sidewall 551' and an opposing sidewall (not seen) each have flat exterior surfaces extending alongside all of ports 561A,B and 562A,B and a maximum thickness between the sidewalls is no greater than approximately 0.3 inch, preferably between approximately 0.22 inch and approximately 0.27 inch.

FIGS. 6A-B further illustrate elongate body 571' extending from housing 54' at a location between first portion 521 and second portion 523' of second housing face 542', and conductor paths routed from each housing contact 533, 501, 502, 503, 504, within housing 54', toward a junction with body 571', in order to accommodate electrical coupling of each of conductors 580 with the corresponding housing contact. With reference to FIG. 6A, dashed lines indicate an alternate location, on second portion 523' of second housing face 242', for the junction between elongate body 571' and housing 54'. Elongate body 571' may be similar in length and construction to that previously described for body 571 of adapter 500.

FIGS. 6A-B further illustrate adapter housing 54' including optional holes 59 that include liner 590, which holes 59 may facilitate securing of adapter 600 to subcutaneous tissue, as previously described for adapter 500. Alternate implant arrangements of device 20 and extensions 117 coupled together by adapter 600 may include those as previously described for device 20 and extensions 117 coupled together by adapter 200.

In the foregoing detailed description, the invention has been described with reference to specific embodiments. However, it may be appreciated that various modifications and changes can be made without departing from the scope of the invention as set forth in the appended claims.

We claim:

1. An adapter for coupling a pair of implantable neurostimulator lead extension plugs to a connector port of a neurostimulator device; each plug of the pair of plugs including first and second connector terminals extending side-by-side; each of the first and second connector terminals of each plug including a terminal pin contact and a contact surface spaced apart from the pin contact along a length of the corresponding connector terminal; the adapter comprising:
   an elongate body and eight elongate conductors extending therein;
   a connector coupled to a first end of the elongate body, the connector including eight contacts, each of the eight connector contacts for electrical coupling with a corresponding device contact mounted within the connector port of the device, and each of the eight connector contacts coupled to a corresponding conductor of the eight elongate conductors; and
   a housing coupled to a second end of the elongate body, the housing including a first sidewall, a second sidewall, a first face extending between the first and second sidewalls, a second face, opposite the first face, extending between the first and second sidewalls, a first pair of housing ports and a second pair of housing ports;
   wherein each port of the first and second pairs of housing ports includes a first housing contact and a second housing contact, each of the first and second housing contacts coupled to a corresponding connector contact via the corresponding conductor extending from the elongate body and into the housing;
   each port of the first pair of housing ports has an opening located on the first housing face and each port of the second pair of housing ports has an opening located on the second housing face; and
   the port openings of each pair of ports provides for insertion of the connector terminals of one of the pair of extension plugs therein for electrical coupling of the pin contact of each plug connector terminal with the corresponding first housing contact, and electrical coupling of the contact surface of each plug connector terminal with the corresponding second housing contact.

2. The adapter of claim 1, wherein each port of the first and second pairs of housing ports includes a longitudinal axis, and all the longitudinal axes are approximately co-planar.

3. The adapter of claim 1, wherein at least one of the first and second housing faces includes a first portion, on which the corresponding pair of port openings is located, and a second portion receding from the first portion at an angle greater than 0 degrees and less than 90 degrees.

4. The adapter of claim 3, wherein the elongate body extends from the housing at a location between the first and second portions of one of the at least one of the first and second housing faces.

5. The adapter of claim 3, wherein the elongate body extends from the housing at a location along the second portion of one of the at least one of the first and second housing faces.

6. The adapter of claim 1, wherein at least one of the first and second housing faces includes a first portion, on which the corresponding pair of port openings is located, and a second portion projecting out from the first portion at an angle of approximately 90 degrees.

7. The adapter of claim 6, wherein the at least one of the first and second housing faces further includes a third portion receding from the second portion at an angle greater than 90 degrees and less than 180 degrees.

8. The adapter of claim 7, wherein the elongate body extends from the housing at a location along the third portion of one of the at least one of the first and second housing faces.

9. The adapter of claim 1, wherein the eight connector contacts are spaced apart from one another along a length of the connector.

10. The adapter of claim 1, wherein the elongate body has a length between approximately 10 centimeters and approximately 20 centimeters.

11. The adapter of claim 1, wherein the elongate body has a length greater than approximately 40 centimeters.

12. The adapter of claim 1, wherein a maximum thickness between the first and second housing sidewalls is no greater than approximately 0.3 inch.

13. The adapter of claim 1, wherein at least one of the first and second housing sidewalls has a relatively flat outer surface extending alongside all of the housing ports.

14. The adapter of claim 1, wherein:
   the first housing contact of a first port of the first pair of housing ports comprises a set screw mounted in a set screw block;
   the second housing face includes a first portion, on which the second pair of port openings is located, and a second portion receding from the first portion at an angle greater than 0 degrees and less than 90 degrees; and
   the housing further includes an access port for the set screw, the access port located on the second portion of the second housing face.

15. The adapter of claim 14, wherein:
the first housing contact of a first port of the second pair of housing ports comprises another set screw mounted in another set screw block;
the first housing face includes a first portion, on which the first pair of port openings is located, and a second portion receding from the first portion of the first housing face at an angle greater than 0 degrees and less than 90 degrees; and
the housing further includes another access port for the other set screw, the other access port located on the second portion of the first housing face.

16. The adapter of claim 1, wherein:
the first housing contact of a first port of the first pair of housing ports comprises a set screw mounted in a set screw block;
the housing further includes a third face extending between the first and second sidewalls and the first and second housing faces, and an access port, for the set screw, located on the third housing face.

17. The adapter of claim 16, wherein:
the first housing contact of a first port of the second pair of housing ports comprises another set screw mounted in another set screw block;
the housing further includes a fourth face, opposite the third housing face, extending between the first and second housing sidewalls and the first and second housing faces, and another access port, for the other set screw, located on the fourth housing face.

18. The adapter of claim 1, wherein:
the first housing contact of each port of the first and second pairs of housing ports comprises a set screw mounted in a set screw block;
the housing further includes an access port for each of the set screws; and
none of the access ports are located along either sidewall of the housing.

19. The adapter of claim 1, wherein the first housing contact of a first port of the first pair of housing ports comprises a set screw mounted in a set screw block, and a shaft of the mounted set screw extends at an angle greater than 0 degrees and less than 90 degrees with respect to the first housing face.

20. The adapter of claim 19, wherein the first housing contact of a first port of the second pair of housing ports comprises another set screw mounted in another set screw block, and a shaft of the other set screw extends at an angle greater than 0 degrees and less than 90 degrees with respect to the second housing face.

21. The adapter of claim 1, wherein the housing further includes a hole extending therethrough from the first sidewall to the second sidewall.

22. The adapter of claim 21, wherein the hole is lined with a reinforcing material.

23. An extension system for coupling an implantable neurostimulator lead to a connector port of a neurostimulator device, the system comprising:
a lead extension including an elongate body, a connector port, coupled to a first end of the elongate body, for receiving a connector terminal of the neurostimulator lead, and an extension plug coupled to a second end of the elongate body, the extension plug including first and second connector terminals extending side-by-side; each of the first and second plug connector terminals including a terminal pin contact and a contact surface spaced apart from the pin contact along a length of the corresponding plug connector terminal; and
an adapter comprising:
an elongate body and eight elongate conductors extending therein;
a connector coupled to a first end of the elongate body, the connector including eight contacts, each of the eight connector contacts for electrical coupling with a corresponding device contact mounted within the connector port of the device, and each of the eight connector contacts coupled to a corresponding conductor of the eight elongate conductors; and
a housing coupled to a second end of the elongate body, the housing including a first sidewall, a second sidewall, a first face extending between the first and second sidewalls, a second face, opposite the first face, extending between the first and second sidewalls, a first pair of housing ports and a second pair of housing ports;
wherein each port of the first and second pairs of housing ports includes a first housing contact and a second housing contact, each of the first and second housing contacts coupled to a corresponding connector contact via the corresponding conductor extending from the elongate body and into the housing;
each port of the first pair of housing ports has an opening located on the first housing face and each port of the second pair of housing ports has an opening located on the second housing face; and
the port openings of each pair of ports provides for insertion of the connector terminals of one of the pair of extension plugs therein for electrical coupling of the pin contact of each plug connector terminal with the corresponding first housing contact, and electrical coupling of the contact surface of each plug connector terminal with the corresponding second housing contact.

24. The system of claim 23, wherein each port of the first and second pairs of adapter housing ports includes a longitudinal axis, and all the longitudinal axes are approximately co-planar.

25. The system of claim 23, wherein at least one of the first and second adapter housing faces includes a first portion, on which the corresponding pair of port openings is located, and a second portion receding from the first portion at an angle greater than 0 degrees and less than 90 degrees.

26. The system of claim 25, wherein the elongate body of the adapter extends from the adapter housing at a location between the first and second portions of one of the at least one of the first and second housing faces.

27. The system of claim 25, wherein the elongate body of the adapter extends from the adapter housing at a location along the second portion of one of the at least one of the first and second housing faces.

28. The system of claim 23, wherein at least one of the first and second housing faces includes a first portion, on which the corresponding pair of port openings is located, and a second portion projecting out from the first portion at an angle of approximately 90 degrees.

29. The system of claim 28, wherein the at least one of the first and second adapter housing faces further includes a third portion receding from the second portion at an angle greater than 90 degrees and less than 180 degrees.

30. The adapter of claim 29, wherein the elongate body of the adapter extends from the adapter housing at a location along the third portion of one of the at least one of the first and second housing faces.

31. The system of claim 23, wherein the eight connector contacts of the adapter are spaced apart from one another along a length of the adapter connector.

32. The system of claim 23, wherein the elongate body of the adapter has a length between approximately 10 centimeters and approximately 20 centimeters.

33. The system of claim 23, wherein the elongate body of the adapter has a length greater than approximately 40 centimeters.

34. The system of claim 23, wherein a maximum thickness between the first and second adapter housing sidewalls is no greater than approximately 0.3 inch.

35. The system of claim 23, wherein at least one of the first and second adapter housing sidewalls has a relatively flat outer surface extending alongside all of the housing ports.

36. The system of claim 23, wherein:
the first housing contact of a first port of the first pair of adapter housing ports comprises a set screw mounted in a set screw block;
the second adapter housing face includes a first portion, on which the second pair of port openings is located, and a second portion receding from the first portion at an angle greater than 0 degrees and less than 90 degrees; and
the adapter housing further includes an access port for the set screw, the access port located on the second portion of the second housing face.

37. The system of claim 36, wherein:
the first housing contact of a first port of the second pair of adapter housing ports comprises another set screw mounted in another set screw block;
the first adapter housing face includes a first portion, on which the first pair of port openings is located, and a second portion receding from the first portion of the first housing face at an angle greater than 0 degrees and less than 90 degrees; and
the adapter housing further includes another access port for the other set screw, the other access port located on the second portion of the first housing face.

38. The system of claim 23, wherein:
the first housing contact of a first port of the first pair of adapter housing ports comprises a set screw mounted in a set screw block;
the adapter housing further includes a third face extending between the first and second housing sidewalls and the first and second housing faces, and an access port, for the set screw, located on the third housing face.

39. The system of claim 38, wherein:
the first housing contact of a first port of the second pair of adapter housing ports comprises another set screw mounted in another set screw block;
the adapter housing further includes a fourth face, opposite the third housing face, extending between the first and second sidewalls and the first and second faces, and another access port, for the other set screw, located on the fourth housing face.

40. The system of claim 23, wherein:
the first housing contact of each port of the first and second pairs of adapter housing ports comprises a set screw mounted in a set screw block;
the adapter housing further includes an access port for each of the set screws; and
none of the access ports are located along either sidewall of the adapter housing.

41. The system of claim 23, wherein the first housing contact of a first port of the first pair of adapter housing ports comprises a set screw mounted in a set screw block, and a shaft of the mounted set screw extends at an angle greater than 0 degrees and less than 90 degrees with respect to the first housing face of the adapter.

42. The system of claim 41, wherein the first housing contact of a first port of the second pair of adapter housing ports comprises another set screw mounted in another set screw block, and a shaft of the other set screw extends at an angle greater than 0 degrees and less than 90 degrees with respect to the second housing face of the adapter.

43. The system of claim 23, wherein the adapter housing further includes a hole extending therethrough from the first sidewall to the second sidewall.

44. The system of claim 43, wherein the hole is lined with a reinforcing material.

* * * * *